(12) United States Patent
Gilson

(10) Patent No.: US 8,857,436 B2
(45) Date of Patent: Oct. 14, 2014

(54) INTERMITTENT LOW-PRESSURE OROTRACHEAL INTUBATION DEVICE

(76) Inventor: Barreto Gilson, Campinas-SP (BR)

(*) Notice: Subject to any disclaimer, the term of this patent is extended or adjusted under 35 U.S.C. 154(b) by 357 days.

(21) Appl. No.: 13/145,512

(22) PCT Filed: Mar. 23, 2009

(86) PCT No.: PCT/BR2009/000080
§ 371 (c)(1),
(2), (4) Date: Jul. 20, 2011

(87) PCT Pub. No.: WO2010/108242
PCT Pub. Date: Sep. 30, 2010

(65) Prior Publication Data
US 2012/0012115 A1   Jan. 19, 2012

(51) Int. Cl.
*A61M 16/04* (2006.01)
*A62B 9/02* (2006.01)
*A61M 16/20* (2006.01)

(52) U.S. Cl.
CPC ........... *A61M 16/04* (2013.01); *A61M 16/0452* (2014.02); *A61M 16/208* (2013.01)
USPC ............. 128/207.16; 128/207.14; 128/207.15

(58) Field of Classification Search
USPC .......................... 128/207.14–207.16, 207.18; 604/99.02–99.04, 102.01–102.03
See application file for complete search history.

(56) References Cited

U.S. PATENT DOCUMENTS

| | | | |
|---|---|---|---|
| 3,707,151 A | 12/1972 | Jackson | |
| 3,709,227 A | 1/1973 | Hayward | |
| 4,278,081 A * | 7/1981 | Jones | 128/207.15 |
| 5,318,021 A | 6/1994 | Alessi | |
| 5,638,813 A * | 6/1997 | Augustine | 128/207.15 |
| 5,765,557 A * | 6/1998 | Warters | 128/207.14 |
| 7,156,090 B2 * | 1/2007 | Nomori | 128/200.26 |

FOREIGN PATENT DOCUMENTS

WO   9966975 A1   12/1999

OTHER PUBLICATIONS

Search Report and Written Opinion for International Patent Application No. PCT/BR2009/000080; May 28, 2010.

* cited by examiner

*Primary Examiner* — Justine Yu
*Assistant Examiner* — Michael Tsai
(74) *Attorney, Agent, or Firm* — B. Aaron Schulman, Esq.; Stites & Harbison, PLLC.

(57) ABSTRACT

An orotracheal intubation device (1) for intermittent low-pressure ventilation of a patient provided with an inflatable cuff (3) including two lines of holes (2,5) communicating with the inflatable cuff and a one-way round valve (4) preventing air flow during inspiration and allowing air flow during expiration.

6 Claims, 2 Drawing Sheets

INTERMITTENT LOW-PRESSURE OROTRACHEAL INTUBATION DEVICE

PRIORITY CLAIM

This patent application is a U.S. National Phase of International Patent Application No. PCT/BR2009/000080, filed Mar. 3, 2009, the disclosure of which is incorporated herein by reference in its entirety.

FIELD

This report is about the detailed description, followed by accompanying images, of a new invention related to a new device for intermittent low-pressure orotracheal intubation. Such device aims at replacing the orotracheal tube currently used for mechanical ventilation of patients who may need such support, either during Internal Care Unit (ICU) stay or for surgery under general anesthesia.

BACKGROUND

The intermittent low-pressure orotracheal intubation device, the subject of this patent, is very interesting commercially because it should replace, with gains, the currently known models of such device which have been used in all hospitals, emergency medical services, private clinics, paramedic medical services, etc. The companies that may be interested in producing this device are the ones that already produce similar orotracheal tubes currently at use.

Currently existing orotracheal tubes have, in most cases, a little balloon at its tip which is introduced through the patient's mouth until it reaches the trachea. This balloon is insufflated using a cuff (or specific insufflator) which is located in the initial tip of the tube. The disadvantage of such tube is the random insufflation of the cuff in non-determined pressure values, so that one may not have the correct control of the insufflating pressure which may hurt the patient.

Such pressure increase of the balloon is transmitted to the tracheal wall which may hurt the patient and damage the tracheal epithelium. The longer the period under intubation, the greater will be the spread of the wall ischemy, thus causing more harm to the patient's trachea.

The present invention has an intermittent low-pressure insufflation of the balloon, thus causing lower pressure on the tracheal wall, less ischemy and less lesions to the tracheal epithelium, granting more comfort and better recovery for the patient.

BRIEF DESCRIPTION OF THE DRAWINGS

Below is a reference to the images following this descriptive report for clarification purposes and better understanding of the device.

DETAILED DESCRIPTION

Figure 1:
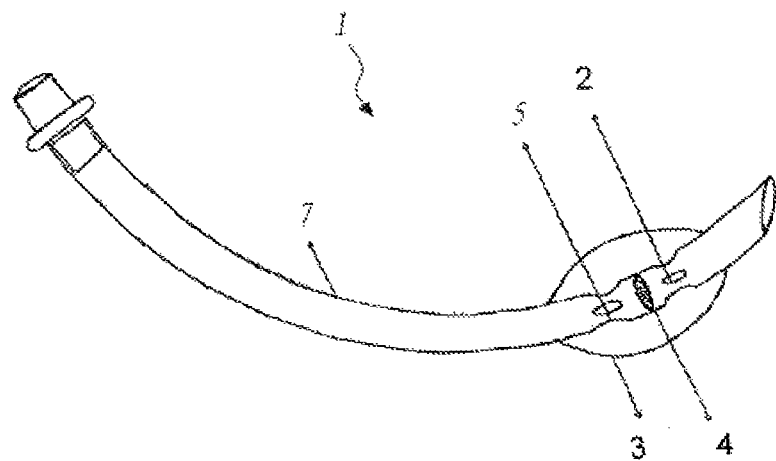
FIG. 1 shows the intermittent low pressure orotracheal tube, or device (1) emphasizing its configuration details: the round holes of line A (5); the round holes of line B (2); the balloon (3) and the one-way valve (4).
Figure 2:
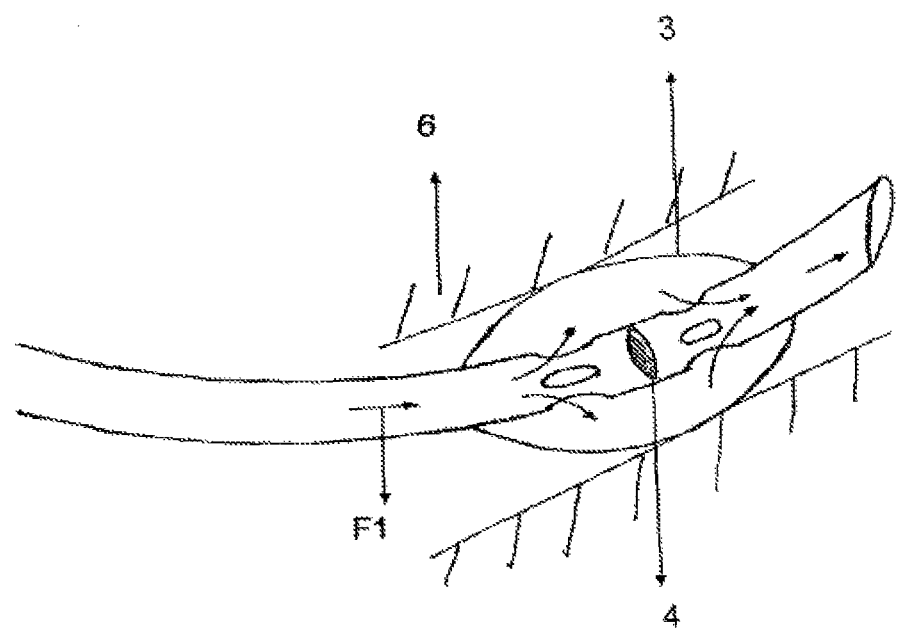
FIG. 2 shows a detail of the insufflated balloon during mechanical inspiration, showing how it works, and emphasizing: the directed air flow (F1); the tracheal wall (6); the balloon (3); the closed one-way valve (4).
Figure 3:
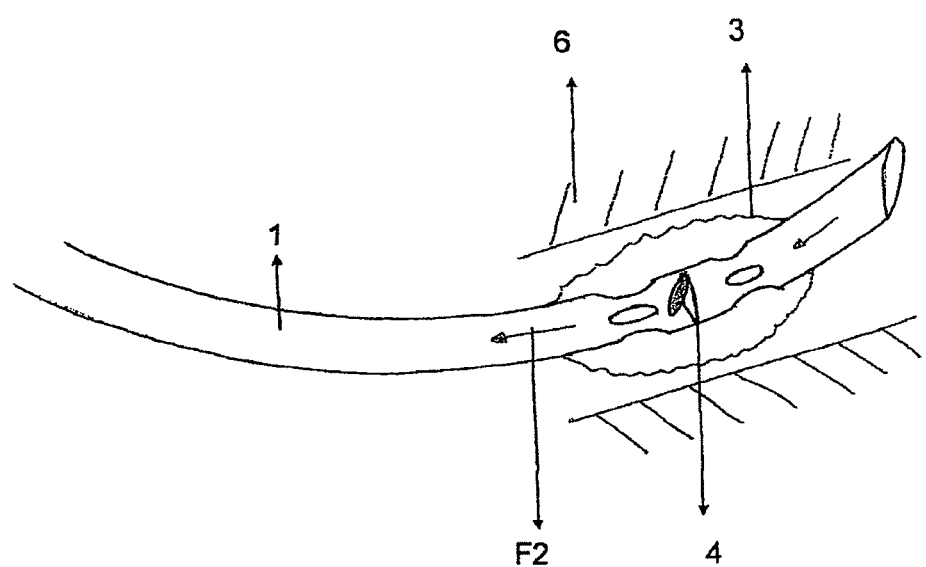
FIG. 3 shows a detail of the uninsufflated balloon during mechanical expiration, emphasizing: the directed air flow (F2); the tracheal wall (6); the uninsufflated balloon (3); and the open one-way valve (4).

Following is a description of the non-restrictive preferred form of the manufacturing of the device subject of this patent, when configuration and application may vary according to each desired model; and the description of one of the possibilities for manufacturing the described object and the way it works.

The intermittent low-pressure orotracheal intubation device (1), the subject of this patent, has a distal balloon (3) located in one of the tips of the tube (1), which causes the closing of the trachea (6) with intermittent controlled and low pressure levels. The insufflation of the balloon (3) is done by the equipment attached to the orotracheal tube, normally a mechanical ventilator, and only takes place during inspiration.

The mechanism granting such intermittent insufflation is made of two lines of holes around the distal portion of the orotracheal tube: a hole line A (5) and a hole line B (2). Inside the tube, between the hole lines (5,2), there is a one-way round valve (4) built in such a way to prevent air flow during inspiration and allow exiting air flow during expiration.

Outside the tube, around and including the two lines of holes (5,2) there is a fixed and malleable plastic balloon (3). During inspiration, the air flow goes through the hole line A (5), causing the distension of the balloon (3) before the air flow escapes through the round holes in line B (2), thus reaching the patient's breathing system.

During expiration, the one-way valve (4), located inside the tube, opens and allows the free flow of air from the lungs back to the equipment. During this phase, there is no pressure in the balloon (3), thus deflating it (Image 3).

There are many advantages to the use of this new orotracheal tube with intermittent flowing and low pressure balloon, among which: the advantage of having the balloon insufflated only during inspiration, allowing blood flow in the wall of the trachea during assisted ventilation, thus granting less harm to the wall of the trachea, directly granting the patient less post-surgery cervical discomfort, with lower risks of harm, like tracheal stenosis in patients under long periods of assisted ventilation in intense care units. Another important advantage is the elimination of one phase of the medical procedure during intubation, i.e. the insufflation of the balloon. Besides eliminating the device called "cuff" of the conventional orotracheal tube and eliminate the need for a syringe for the filling up of the balloon, it allows immediate and efficient ventilation right after the intubation.

Therefore, based on the above mentioned configuration and working characteristics, we can clearly see that the INTERMITTENT LOW-PRESSURE OROTRACHEAL INTUBATION DEVICE is a new state-of-the-art device surrounded by unprecedented novelty, practicality, application, performance and improvements that granted it the status of Utility Model Patent Privilege.

The invention claimed is:

1. An intermittent low-pressure orotracheal intubation device adapted for ventilating a patient comprising:
   (a) an endotracheal tube having a proximal end with an opening and a distal end with an opening, said distal end adapted to project into the trachea and said proximal end adapted to project from the oral cavity;
   (b) an inflatable balloon coupled to the tube near the distal end of said tube, said inflatable balloon surrounding a portion of said tube;
   (c) a one-way valve located inside the portion of the tube surrounded by said inflatable balloon;

(d) a first port in said tube, proximal to said one-way valve, in fluid communication with said inflatable balloon;

(e) a second port in said tube, distal to said one-way valve, in fluid communication with said inflatable balloon;

wherein during inspiration air is forced into said tube from the proximal end, said one-way valve is closed forcing the air to exit said first port and distend said balloon, the air then exits the distended balloon via said second port;

wherein the distention of said balloon is adapted to occlude the trachea to prevent air from escaping up the trachea during inspiration; and wherein during expiration said one-way valve is open to allow air to flow through the tube in order to substantially eliminate pressure by the balloon against the trachea.

2. The device of claim 1, wherein said first and second ports are a line of holes in said tube.

3. The device of claim 1, wherein an equipment is attached to the proximal end of said tube to force air into said tube.

4. The device of claim 2, wherein said equipment is a mechanical ventilator.

5. The device of claim 1, wherein said inflatable balloon is inflatable and deflatable.

6. The device of claim 1, wherein said inflatable balloon is a malleable plastic balloon.

* * * * *